United States Patent [19]
Payne

[11] Patent Number: 5,558,816
[45] Date of Patent: Sep. 24, 1996

[54] STABLE LIQUID COMPOSITIONS AND THEIR USE

[75] Inventor: John D. Payne, Rossendale, United Kingdom

[73] Assignee: Zeneca Limited, London, England

[21] Appl. No.: 492,003

[22] PCT Filed: Jan. 19, 1994

[86] PCT No.: PCT/GB94/00100

§ 371 Date: Jul. 19, 1995

§ 102(e) Date: Jul. 19, 1995

[87] PCT Pub. No.: WO94/16564

PCT Pub. Date: Aug. 4, 1994

[30] Foreign Application Priority Data

Jan. 19, 1993 [GB] United Kingdom .................. 9300936

[51] Int. Cl.[6] .................. A01N 43/80; C07D 275/06
[52] U.S. Cl. .................. 252/400.62; 514/373; 548/209
[58] Field of Search .................. 252/400.62; 514/373; 548/209

[56] References Cited

U.S. PATENT DOCUMENTS

| | | | |
|---|---|---|---|
| 4,188,376 | 2/1980 | Payne et al. | 424/173 |
| 5,160,666 | 11/1992 | Lindner et al. | 252/402 |
| 5,185,356 | 2/1993 | Backhouse et al. | 514/372 |

FOREIGN PATENT DOCUMENTS

| | | |
|---|---|---|
| 208488 | 1/1987 | European Pat. Off. . |
| 482328 | 4/1992 | European Pat. Off. . |
| 2087938 | 12/1971 | France . |
| 2004747 | 4/1979 | United Kingdom . |

*Primary Examiner*—Joseph K. McKane
*Assistant Examiner*—Laura R. Cross
*Attorney, Agent, or Firm*—Cushman Darby & Cushman, LLP

[57] ABSTRACT

Stable composition of 1,2-benzisothiazolin-3-one (BIT) in dipropylene glycol having lower pH and lower viscosity than known compositions. The BIT is present as an alkali metal salt obtained by reacting 0.75 to 1.07 moles alkali metal hydroxide with one mole BIT.

9 Claims, No Drawings

STABLE LIQUID COMPOSITIONS AND THEIR USE

This application is a 371 of PCT/GB 94/0100 filed Jan. 19, 1994.

The present invention relates to a stable liquid composition comprising an alkali metal salt of 1,2-benzisothiazolin-3-one and dipropylene glycol having a lower pH and lower viscosity than those hitherto known.

1,2-benzisothiazolin-3-one (referred to hereinafter as BIT) is an established industrial biocide and is particularly effective in protecting aqueous media against microbiological spoilage. It is particularly effective as a bactericide and is especially suited to the protection of latices. Thus one of its major uses is as an in-can preservative for the preservation of acrylic and acrylate paint emulsions.

BIT has low aqueous solubility and can cause sensitization in some individuals. Consequently, for ease of handling and to reduce handling risks, it has been formulated as an aqueous dispersion and also as a stable solution in an amine solvent as disclosed in UK 1,191,253 and UK 1,330,531. For some applications, these amine formulations are not attractive and are rarely used for indirect food contact applications, such as for instance for use in water-based adhesives which may be used in the food packaging industry, because the amines are volatile and tend to have an unpleasant odour. Furthermore, amine solutions of BIT may not be suitable for use as biocides in in-can preservation of latices because amine solvents may cause yellowing of the latex. Amines are also capable of reacting with and deactivating certain biocides and this further limits the use of amine formulations of BIT when used with such biocides.

To avoid these problems associated with amines, BIT is now generally formulated as an alkali metal salt in one or more water miscible solvents such as dipropylene glycol as disclosed in U.S. Pat. No. 4,188,376. Such formulations are stable solutions which withstand freeze-thaw temperature cycling, and even if frozen recover on warming to re-generate a stable solution. Formulations of this type containing 20% BIT, and 658% dipropylene glycol, the remainder being water wherein the BIT has been converted to sodium-BIT by reacting 1.1 moles sodium hydroxide with 1 mole BIT as described in Example 1 of U.S. Pat. No. 4,188,376, have been available commercially for many years as Proxel GXL (Proxel is a registered trade mark of ICI PLC). These formulations have proved highly successful and withstand all but the most extreme of low temperatures. However, these glycol formulations suffer from high viscosity at lower temperatures even when remaining fluid, and this causes problems in metering the correct dosage, especially by pumping. A further disadvantage of such formulations is their high pH, normally pH 12 or above, which can cause 'pH-shock' and coagulation when added to a medium to be protected, such as an emulsion paint or latex, owing to the different pH of the medium. The high viscosity and high pH are caused by the combination of the amount and type of solvent employed and also the amount of alkali both of which have hitherto been considered necessary to produce stable solutions of sodium-BIT. Indeed, in all the working examples of U.S. Pat. No. 4,188,376 a 10% excess of sodium hydroxide has been used relative to BIT in making the sodium salt. We have now found that the use of such high levels of sodium hydroxide is unnecessary and that stable solutions can be obtained even when using less than stoichiometric amounts of alkali. It has also been found that the amount of dipropylene glycol can also be reduced, which further reduces the viscosity without adversely affecting the storage properties.

According to the invention there is provided a stable composition comprising from 5 to 25% by weight of BIT and from 40% to 60% dipropylene glycol, wherein the BIT is present as an alkali metal salt formed by reacting from 0.75 to 1.07 moles alkali metal hydroxide with one mole of BIT.

The remainder of the composition may be water, one or more solvents selected from propylene glycol, dipropylene glycol, tripropylene glycol, $C_{1-4}$-alkyl carbitols and $C_{1-4}$-alkanols.

The alkali metal hydroxide, may be one or more of lithium, sodium or potassium hydroxide, but especially sodium hydroxide. The preferred amount of BIT in the composition is preferably from 10 to 25%, more preferably from 15 to 25% and especially from 18 to 23% by weight, and more especially about 20% based on the total weight of the composition.

The amount of dipropylene glycol in the composition is preferably from 50 to 65%, more preferably from 50 to 60% and especially from 52 to 58%, by weight relative to the total weight of the composition. The alkali metal hydroxide is preferably from 0.80 to 1.05 moles per mole of BIT, more preferably from 0.95 to 1.02 moles per mole of BIT and especially 0.98 to 1.01 moles. It is particularly preferred to use stoichiometric amounts of BIT and alkali metal hydroxide or as close to stoichiometric amounts as are practically attainable on an industrial scale of manufacture.

Examples of $C_{1-4}$-lower carbitols are methyl and ethyl carbitol and examples of $C_{1-4}$-alkanols are methanol, ethanol, n-propanol and isopropanol. Preferably, the composition contains no other solvents other than dipropylene glycol and water.

Particularly stable solutions have been obtained containing by weight 20% BIT, 55% dipropylene glycol and from 4.2 to 5.7% sodium hydroxide, the remainder being water. In such solutions the amount of sodium hydroxide is from 0.8 to 1.07 moles for each mole of BIT. Such solutions have a pH between about 8.9 and about 10, and a viscosity measured at 18° C. between about 60 and about 180 mPa.s. These solutions have been found to be readily pourable and pumpable at lower temperatures and to exhibit no adverse properties such as separation when stored at elevated temperatures of about 40° C., lower temperatures of about −13° C. or when repeatedly cycled at temperatures between −13° C. and 40° C. over a 24 hour period. The solutions are also stable at low temperatures even when the solution is seeded with crystals of Na-BIT.

In order to avoid handling and drying the BIT, the present composition may be made directly from an aqueous paste of BIT e.g. a press paste, which typically contains from 20% to 35% by weight water. The composition may be made by dissolving the alkali metal hydroxide in a mixture of dipropylene glycol and water and heating up to 80° C. to effect solution. The BIT press paste may then be added to the basic solvent and the mixture again stirred at a temperature up to 80° C. to dissolve the BIT. The solution may then be optionally filtered either warm or after cooling to ambient conditions. Filtration at ambient temperatures is more readily effected with the present composition than with the composition described in U.S. Pat No. 4,188,376 because of the lower viscosity of the present composition.

The compositions of the present invention exhibit similar control of micro-organisms as do existing formulations of BIT and can, therefore, be used to prevent microbial spoilage in media where micro-organisms grow.

The invention is illustrated by the following Examples in which all parts and percentages are by weight unless stated to the contrary.

EXAMPLES 1 TO 5 AND COMPARATIVE EXAMPLE A

Sodium hydroxide (5.8 parts; 1.09 moles) per mole BIT was added to dipropylene glycol (150 parts) and water (18.9 parts) and heated to 70° C. and stirred to dissolve the sodium hydroxide. BIT press paste (66.6 parts equivalent to 50 parts dry BIT; 0.1325 moles) was added to the alkaline solution and stirred at 50° C. to dissolve the BIT. The solution was adjusted to 250 parts by addition of water, then filtered, and contained by weight 20% BIT and 60% dipropylene glycol, the remainder being water and where the BIT is present as Na-BIT formed from 1.09 moles sodium hydroxide for each mole of BIT. The solution had a pH of 11.7, and a viscosity at 18° C. of 226 mPa.s.

Similar solutions were prepared using lower amounts of sodium hydroxide as detailed in Table 1 below, and the pH and viscosity of each recorded.

TABLE 1

| Example or Comp Example | BIT (%) | (a) dpg (%) | NaOH[b] | Molar Ratio of NaOH to BIT | pH | Viscosity (18° C., mP · s) |
|---|---|---|---|---|---|---|
| A | 20 | 60 | 5.8 | 1.09 | 11.7 | 226 |
| 1 | 20 | 60 | 5.7 | 1.075 | 9.8 | 197 |
| 2 | 20 | 60 | 5.6 | 1.057 | 9.6 | 193 |
| 3 | 20 | 60 | 5.4 | 1.019 | 9.3 | 171 |
| 4 | 20 | 60 | 5.3 | 1.0 | 9.0 | 191 |
| 5 | 20 | 60 | 5.2 | 0.98 | 8.9 | 200 | a) dpg is dipropylene glycol

This column in Tables 1, 2, 3 and 6 represents the amount of NaOH relative to 50 parts BIT.

These solutions all exhibited good storage properties when held at 40° C., −13° C. and when cycled between −13°C and 40° C. over repeated 24 hour intervals. Storage properties at low temperatures were unaffected even after seeding with Na-BIT crystals.

EXAMPLES 6 TO 10 AND COMPARATIVE EXAMPLE B

These examples were made in similar manner to those described in Examples 1 to 5, except that 137.5 parts of dipropylene glycol (dpg) were used instead of the 150 parts and the water was increased according. These solutions all contained 55% (w/w) dipropylene glycol. Details of these solutions are given in Table 2 below.

TABLE 2

| Example or Comp Example | BIT (%) | (a) dpg (%) | NaOH[b] | Molar Ratio of NaOH to BIT | pH | Viscosity (18° C., mP · s) |
|---|---|---|---|---|---|---|
| B | 20 | 55 | 5.8 | 1.09 | 10.6 | 140 |
| 6 | 20 | 55 | 5.7 | 1.075 | 10.0 | 114 |
| 7 | 20 | 55 | 5.6 | 1.057 | 9.8 | 110 |
| 8 | 20 | 55 | 5.4 | 1.019 | 9.6 | 116 |
| 9 | 20 | 55 | 5.3 | 1.0 | 9.5 | 105 |
| 10 | 20 | 55 | 5.2 | 0.98 | 9.4 | 99 |

These examples all exhibited similar storage stability to Examples 2 to 5.

EXAMPLES 11 TO 15 AND COMPARATIVE EXAMPLE C

These examples were made in similar manner to those described in Examples 1 to 5 except that 125 parts dipropylene glycol (dpg) were used in place of the 150 parts and the water was increased accordingly. These solutions all contained 50% (w/w) dipropylene glycol. Details of the solutions are given in Table 3.

TABLE 3

| Example or Comp Example | BIT (%) | (a) dpg (%) | NaOH[b] | Molar Ratio of NaOH to BIT | pH | Viscosity (18° C., mP · s) |
|---|---|---|---|---|---|---|
| C | 20 | 50 | 5.8 | 1.09 | 10.1 | 76 |
| 11 | 20 | 50 | 5.7 | 1.075 | 9.9 | 64 |
| 12 | 20 | 50 | 5.6 | 1.057 | 9.5 | 69 |
| 13 | 20 | 50 | 5.4 | 1.019 | 9.3 | 64 |
| 14 | 20 | 50 | 5.3 | 1.0 | 9.2 | 61 |
| 15 | 20 | 50 | 5.2 | 0.98 | 9.1 | 61 |

These examples all exhibited good stability when stored at 40° C. and when repeatedly cycled between −13° C. and 40° C. over a 24 hour interval, even when seeded with Na-BIT crystals when cold. When stored at −13° C., examples 11 to 15, and comparative example C all froze, but complete solution was obtained when the samples returned to ambient temperatures (about 18° C.).

EXAMPLES 16 TO 21

Example 9 was repeated except that the amount of dipropylene glycol (dpg) was varied from 40% to 65% by weight with a corresponding adjustment of the amount of water to 100%. These samples all contained 20% BIT where the BIT is present as Na-BIT formed with stoichiometric amounts of sodium hydroxide. These experiments were carried out in triplicate using three different samples of BIT press paste. The viscosity and appearance of the solutions at −13° C. is given in Table 4.

TABLE 4

| Example | dpg | Viscosity | | | Appearance of solution at −13° C. |
|---|---|---|---|---|---|
| 16 | 40 | 34, | 31 | 36 | all frozen |
| 17 | 45 | 42, | 44 | 60 | all frozen |
| 18 | 50 | 61, | 68 | 97 | all frozen |
| 19 | 55 | 110, | 111 | 175 | all mobile |
| 20 | 60 | 182, | 194 | 334 | two mobile, one thick |
| 21 | 65 | 474, | 467 | — | all thick or very thick |

Examples 16 to 18 all recovered on warming.

EXAMPLE 22

The effect of temperature on the viscosity of Example 9 was measured and compared with a commercial sample of Proxel GXL. Example 9 had a pH of 9.5 and Proxel GXL had a pH of 12.0. The viscosities are recorded in Table 5.

TABLE 5

| | Viscosity at temp °C. | | | | | | |
|---|---|---|---|---|---|---|---|
| Sample | 0 | 4 | 8 | 14 | 17 | 21 | 25 |
| Example 9 | — | 457 | 307 | 222 | 156 | 123 | 97 |
| GXL | 5000 | 3100 | 2350 | 1500 | 1200 | 850 | 600 |

Example 9 is clearly easier to dispense at low temperature. This particular sample was also stored outside for 3 months during the winter and exhibited no adverse properties such as separation or precipitation of the Na-BIT.

EXAMPLES 23 TO 25 AND COMPARATIVE EXAMPLES D AND E

Example 10 was repeated using a different batch of BIT press paste to give formulations containing 20% by weight BIT and 55% dispropylene glycol but with differing ratios of sodium hydroxide relative to BIT. The properties of the formulations obtained is given in Table 6 below.

TABLE 6

| Example of Comp Example | NAOH[b] | Moles Ratio of NaOH to BIT | pH | Viscosity (18° C. mP15) | Appearance (c) |
|---|---|---|---|---|---|
| 23 | 5.3 | 1.0 | 9.64 | 120 | No ppt |
| 24 | 4.8 | 0.9 | 9.13 | 136 | No ppt |
| 25 | 4.2 | 0.8 | 8.90 | 132 | No ppt |
| D | 3.7 | 0.7 | — | — | Ppt |
| E | 3.2 | 0.6 | — | — | Heavy ppt | c) The presence of a precipitate (ppt) was determined after storage for 7 weeks whilst the temperature was repeatedly cycled between −13 and 40° C..

I claim:

1. A stable composition comprising from 5 to 25% by weight of 1,2-benzisothiazolin-3-one (BIT) and from 40 to 68% dipropylene glycol wherein the BIT is present as an alkali metal salt formed by reacting from 0.75 to 1.07 moles alkali metal hydroxide with one mole of BIT.

2. A composition as claimed in claim 1 wherein the alkali metal hydroxide is one or more of lithium, sodium or potassium hydroxide.

3. A composition as claimed in either claim 1 or claim 2 which contains from 15 to 25% by weight BIT.

4. A composition as claimed in claim 1 which contains from 50 to 58% by weight dipropylene glycol.

5. A composition as claimed in claims 1 which contains from 0.80 to 1.05 moles of alkali metal hydroxide per mole BIT.

6. A composition as claimed in claim 1 which contains from 0.95 to 1.02 moles of alkali metal hydroxide per mole of BIT.

7. A composition as claimed in claim 1 which contains substantially stoichiometric amounts of alkali metal hydroxide and BIT.

8. A composition as claimed in claim 1 having a pH from 8.9 to 10.0.

9. A composition as claimed in claim 1 having a viscosity from about 60 to about 180 mPa.s at 18° C.

* * * * *